United States Patent
Norman et al.

(10) Patent No.: US 8,313,807 B2
(45) Date of Patent: Nov. 20, 2012

(54) HIGH COORDINATION SPHERE GROUP 2 METAL β-DIKETIMINATE PRECURSORS

(75) Inventors: John Anthony Thomas Norman, Encinitas, CA (US); Xinjian Lei, Vista, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 643 days.

(21) Appl. No.: 12/535,192

(22) Filed: Aug. 4, 2009

(65) Prior Publication Data
US 2010/0173075 A1    Jul. 8, 2010

Related U.S. Application Data

(60) Provisional application No. 61/086,341, filed on Aug. 5, 2008.

(51) Int. Cl.
C23C 16/00 (2006.01)
C07C 257/00 (2006.01)
C09B 67/00 (2006.01)

(52) U.S. Cl. .................. 427/255.36; 564/278; 564/279; 106/287.21; 427/255.31

(58) Field of Classification Search ............ 427/255.31, 427/255.36; 564/278, 279; 106/287.21
See application file for complete search history.

(56) References Cited

U.S. PATENT DOCUMENTS

| | | |
|---|---|---|
| 2006/0292303 A1 | 12/2006 | Millward et al. |
| 2006/0292873 A1 | 12/2006 | Millward et al. |

OTHER PUBLICATIONS

Anthony G. Avent et al, Dimerization of B-diketiminato calcium complexes through dihapto-acetylide litigation, Organometallics 2005, 24, pp. 1184-1188.
Anthony G. Avent et al, Reactivity of [HC{(C(Me)N(Dipp))}2-Ca{N(SiMe3)2}(THF)] (Dipp = C6H3 . . . , J. Organ. Chemistry 691, 2006, pp. 1242-1250.
Malcolm H. Chisholm et al, Well-defined calcium initiators for lactide polymerization, Inorg. Chem. 2004, 43, No. 21, pp. 6717-6725.
Hani M. El-Kaderi et al, Sandwich complexes of the heavier alkaline earth metals containing . . . , Organometallics 2004, 23, pp. 4995-5002.
Sjoerd Harder, Homoleptic B-diketiminato complexes of the alkaline-earth metals: trends in the . . . , Organometallics 2002, 21, pp. 3782-3787.
Christian Ruspic et al, Big ligands for stabilization of small functionalities in calcium chemistry, Inorg. Chem. 2007, 46, pp. 10426-10433.
S.G. McGeachin, Synthesis and properties of some B-diketimines derived from acetylacetone, and their metal complexes, Canadian Journal of Chemistry, vol. 46, 1968, pp. 1903-1912.
Kyung-Ho Park et al, Routes to N,N'-unsymmetrically substituted 1,3-diketimines, J. Org. Chem. 2005, 70, pp. 2075-2081.

*Primary Examiner* — Porfirio Nazario Gonzalez
(74) *Attorney, Agent, or Firm* — Rosaleen P. Morris-Oskanian

(57) ABSTRACT

The present invention is directed to high coordination sphere Group 2 metal β-diketiminate compositions, such as bis(N-(2,2-methoxyethyl)-4-(2,2-methoxyethylimino)-2-penten-2-aminato) barium; and the deposition of the metals of such metal ligand compositions by chemical vapor deposition, pulsed chemical vapor deposition, molecular layer deposition or atomic layer deposition to produce Group 2 metal containing films, such as barium strontium titanate films or strontium titanate films or barium doped lanthanate as high k materials for electronic device manufacturing.

17 Claims, 1 Drawing Sheet

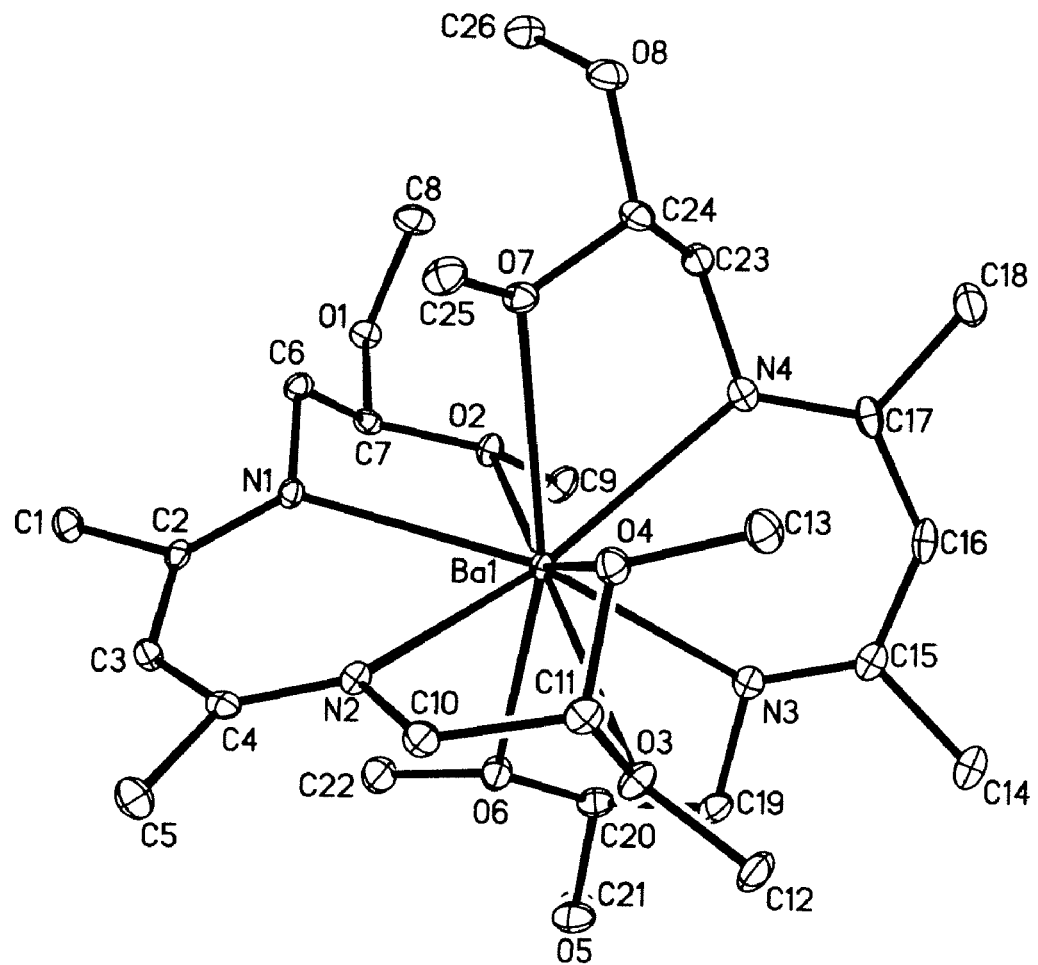

HIGH COORDINATION SPHERE GROUP 2 METAL β-DIKETIMINATE PRECURSORS

CROSS REFERENCE TO RELATED APPLICATION

The present patent application claims the benefit of U.S. Provisional Patent Application Ser. No. 61/086,341 filed Aug. 5, 2008.

BACKGROUND OF THE INVENTION

The semiconductor fabrication industry continues to explore metal containing precursors for chemical vapor deposition processes including atomic layer deposition for fabricating conformal metal containing films on substrates such as silicon, metal nitride, metal oxide and other metal-containing layers using these metal-containing precursors. Barium and strontium containing precursors are especially sought after for the deposition of thin barium and strontium oxide containing films for advanced memory device manufacture. The prior art has attempted to provide precursors for these applications, as set forth below. However, none of the metal complexes in the prior art share the special characteristic of the complexes disclosed in this invention.

RELEVANT PRIOR ART INCLUDES

Avent, A. G., M. R. Crimmin, M. S. Hill and P. B. Hitchcock (2005). "Dimerization of beta-Diketiminato Calcium Complexes through Dihapto-Acetylide Ligation." Organometallics 24(6): 1184-1188.

Avent, A. G., M. R. Crimmin, M. S. Hill and P. B. Hitchcock (2006). "Reactivity of [HC{(C(Me)N(Dipp))}$_2$Ca{N(SiMe$_3$)$_2$}(THF)] (Dipp=2,6-$^i$Pr$_2$C$_6$H$_3$) with C—H acids: Synthesis of heteroleptic calcium η$^5$-organometallics." Journal of Organometallic Chemistry 691(6): 1242-1250.

Chisholm, M. H., J. C. Gallucci and K. Phomphrai (2004). "Well-Defined Calcium Initiators for Lactide Polymerization." Inorg. Chem. 43(21): 6717-6725.

El-Kaderi, H. M. and M. J. W. Heeg, C. H.; (2004). "Sandwich Complexes of the Heavier Alkaline Earth Metals Containing 5-Diketiminato Ligand Sets." Organometallics 23: 4995-5002.

Harder, S. (2002). "Homoleptic beta-Diketiminato Complexes of the Alkaline-Earth Metals Trends in the Series Mg, Ca, Sr, and Ba." Organometallics 21(18): 3782-3787.

Millward, D. and T. Quick (2006). "Beta-diketiminate ligand sources and metal-containing compounds thereof, and systems and methods including same." US2006/0292303A1.

Millward, D., S. Uhlenbrock and T. Quick (2006). "Unsymmetrical ligand sources, reduced symmetry metal-containing compounds, and systems and methods including same." US2006/0292873A1.

Ruspic, C. and S. Harder (2007). "Big Ligands for Stabilization of Small Functionalities in Calcium Chemistry." Inorg. Chem. 46(24): 10426-10433.

McGeachin, Canadian Journal of Chemistry, p. 1903, Vol. 46, 1968.

Park, K. H. and Marshall, W. J. (2005), *J. Org. Chem.* 70, (6), 2075-2081.

BRIEF SUMMARY OF THE INVENTION

The present invention is directed to high coordination sphere Group 2 metal diiminate compositions, for example bis(N-(2,2-bis(methoxy)ethyl)-4-(2,2-bis(methoxy)ethylimino)-2-penten-2-aminato) barium; and the deposition of group 2 metal containing films from such metal complex compositions by chemical vapor deposition, pulsed chemical vapor deposition, molecular layer deposition or atomic layer deposition. Exemplary films include but are not limited to barium, strontium titanate ternary films or strontium titanate binary films for electronic materials device manufacturing.

BRIEF DESCRIPTION OF THE DRAWING

FIG. 1 is the molecular structure of bis(N-(2,2-bis(methoxy)ethyl)-4-(2,2-bis(methoxy)ethylimino)-2-penten-2-aminato) barium as characterized by X-ray single crystal analysis.

DETAILED DESCRIPTION OF THE INVENTION

In contrast to the prior art precursors described above, the compounds of the present invention have aliphatic side chains attached to the nitrogen atoms of a β-diketimine ligand functionalized groups with oxygen and nitrogen atoms. These groups, being anchored to the main body of the β-diketimine ligand can then coordinate to the metal center to provide a large coordination sphere around the metal center. Consequently, this stabilizes the complex and permits monomeric metal complexes to form, especially in the case of barium, which has a tendency to form dimeric, trimeric, tetrameric or polymeric complexes of lesser utility as precursors due to their high molecular weight and extremely low vapor pressure. In the prior arts mentioned above, when β-diketimine ligands are used for Group 2 metal presursors, the groups attached to the β-diketimine nitrogen atoms are simple alkyl groups or alkyl substituted aromatics with no coordinating nitrogen or oxygen atoms.

For instance, in the case where the ligand anion [MeC(NCMe$_3$)CHC(HNCMe$_3$)Me]— coordinates to barium, there are no coordinating oxygen atoms and no additional nitrogen atoms beyond the nitrogen atoms of the β-diketimine ligand.

By contrast, the precursors of the present invention are based upon diketimine ligands that provide an array of coordinating oxygen and nitrogen groups, which can wrap around and encapsulate the metal center.

This invention is directed to metal containing polydentate 6-diketiminates and their solutions for vapor delivery by direct liquid injection, wherein the polydentate β-diketiminates incorporate nitrogen or oxygen functionality by attaching them to the imino groups, as metal coordinating side chains. It also includes a novel method of synthesizing diketiminate ligands in high yield and high purity which avoids the use of toxic alkylating agents, such as triethyloxonium tetrafluoroborate (McGeachin, Canadian Journal of Chemistry, p. 1903, Vol. 46, 1968) or other corrosive and toxic reagents, such as PCI$_5$ or dimethylsulfate, (Park, J. Org. Chem., 2005, 70, 2075-2081) and, importantly, permits the facile synthesis of diketiminate ligands, which bear coordinating atoms in addition to the nitrogen atoms of the diketiminate unit.

Thus, the synthetic problems and complications arising from unwanted O and N alkylation occurring on the coordinating side chains by using the above mentioned published procedures to make the new molecules of this disclosure are eliminated. In this way, previously unreported diketiminate ligands are made for the first time using the novel synthesis of the present invention. The new β-diketimines include: MeC(NCH$_2$CH(OMe)$_2$)CHC(NHCH$_2$CH(OMe)$_2$)Me; MeC (NCH$_2$CH$_2$N(CH$_3$)$_2$)CHC(NH CH$_2$CH$_2$N(CH$_3$)$_2$)Me; and MeC(NCH$_2$CH$_2$OMe)CHC(NHCH$_2$CH$_2$OMe)Me.

The new metal complexes of this disclosure are characterized by β-diketimine and ketoimine ligands, which contain additional coordinating atoms beyond the two nitrogen atoms of the diimine ligand, so as to provide a coordination sphere for the metal center. In this way, the entire coordination sphere is an integral part of the structure of the resulting metal complex. The polydentate metal β-diketiminates are selected from the group represented by the structures:

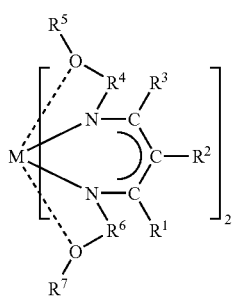

A wherein M is a Group 2 metal selected from the group consisting of magnesium, calcium, strontium, barium and radium, preferably strontium and barium. A variety of organo groups may be employed as for example wherein $R^{1,3}$ are individually selected from the group consisting of hydrogen, alkyl, fluoroalkyl, alkoxy, and fluoroalkoxy having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy having from 1 to 10 carbon atoms, nitro, acyl, halogen and aryl having from 6 to 10 carbon atoms; $R^{4,6}$ are individually selected from the group consisting of alkyl and fluoroalkyl having from 1 to 10 carbon atoms, and aryl having from 6 to 10 carbon atoms, preferably $R^{4,6}$ contains 2 or 3 carbon atoms, thus making a five- or six-member coordinating ring to the metal center; $R^{5,7}$ are individually selected from the group consisting of alkyl and fluoroalkyl having from 1 to 10 carbon atoms, cycloaliphatic and aryl having from 4 to 10 carbon atoms, and they can be connected to form a ring containing carbon, oxygen, or nitrogen atoms. In addition, groups $R^5$ or $R^4$ can be connected to $R^6$ and $R^7$ of the same diketimine ligand or to $R^4$, $R^5$, $R^6$ and $R^7$ of the other diketimine ligand. Similarly, $R^6$ and $R^7$ can be connected to the same groups in the other ligand. In addition, cyclic groups can also be formed by connecting $R^1$ to $R^2$, $R^6$ or $R^7$; $R^3$ to $R^2$, $R^4$ or $R^5$; $R^1$ to $R^2$, $R^3$ to $R^2$.

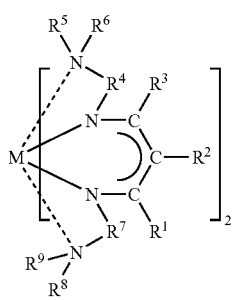

B wherein M is a Group 2 metal selected from the group consisting of magnesium, calcium, strontium, barium, preferably strontium and barium. A variety of organo groups may be employed as for example wherein $R^{1,3}$ is selected from the group consisting of hydrogen, alkyl, fluoroalkyl, alkoxy, and fluoroalkoxy having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy, having from 1 to 10 carbon atoms, nitro, acyl and aryl having from 6 to 10 carbon atoms. $R^1$, $R^2$ and $R^3$ can also be connected to form ring structures. $R^{4,7}$ are individually selected from the group consisting of alkyl and fluoroalkyl having from 1 to 10 carbon atoms, and aryl having from 6 to 10 carbon atoms, preferably $R^{4,7}$ contains 2 or 3 carbon atoms, thus making a five- or six-member coordinating ring to the metal center; $R^{5,6,8,9}$ are individually selected from the group consisting of alkyl and fluoroalkyl having from 1 to 10 carbon atoms, cycloaliphatic and aryl having from 4 to 10 carbon atoms, and they can be connected to form a ring containing carbon, oxygen, or nitrogen atoms. In addition, groups $R^4$, $R^5$ and $R^6$ can be connected to $R^7$, $R^8$ and $R^9$ of the same diketimine ligand or to $R^4$, $R^5$, $R^6$, $R^7$, $R^8$ or $R^9$ of the other diketimine ligand. Similarly, $R^7$, $R^8$ and $R^9$ can be connected to the same groups in the other ligand. In addition $R^1$ can be connected to $R^2$, $R^7$, $R^8$ or $R^9$ and $R^3$ can be connected to $R^4$, $R^5$ and $R^6$.

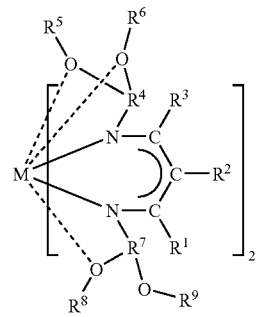

C wherein M is a Group 2 metal selected from the group consisting of magnesium, calcium, strontium, barium or radium, preferably strontium and barium. A variety of organo groups may be employed as for example wherein $R^{1,3}$ is selected from the group consisting of hydrogen, alkyl, and fluoroalkyl having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy having from 1 to 10 carbon atoms, nitro, acyl, halogen and aryl having from 6 to 10 carbon atoms. $R^1$, $R^2$ and $R^3$ can also be connected to form rings. $R^{4,7}$ are individually selected from the group consisting of alkyl and fluoroalkyl having from 1 to 10 carbon atoms, and aryl having from 6 to 10 carbon atoms. Preferably $R^{4,7}$ contains 2 or 3 carbon atoms, thus making a five- or six-member coordinating ring to the metal center; $R^{5,6,8,9}$ are individually selected from the group consisting of alkyl and fluoroalkyl having from 1 to 10 carbon atoms, cycloaliphatic and aryl having from 4 to 10 carbon atoms, and they can be connected to form a ring containing carbon, oxygen, or nitrogen atoms. Groups $R^4$, $R^5$ or $R^6$ can be connected to $R^7$, $R^8$ or $R^9$ of the same diketimine ligand or to $R^4$, $R^5$, $R^6$, $R^7$, $R^8$ or $R^9$ of the other diketimine ligand. Similarly, $R^7$, $R^8$ or $R^9$ can be connected to the same groups in the other ligand. In addition, $R^1$ can also be attached to $R^2$, $R^7$, $R^8$ and $R^9$; $R^3$ can be attached to $R^2$, $R^4$, $R^5$ or $R^6$.

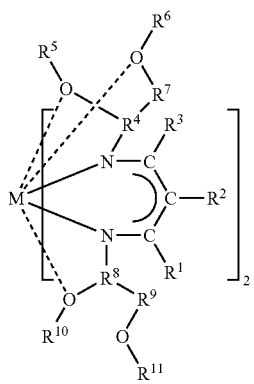

D wherein M is a Group 2 metal selected from the group consisting of magnesium, calcium, strontium, barium or radium, preferably strontium and barium. A variety of organo groups may be employed as for example wherein $R^{1,3}$ is selected from the group consisting of alkyl, fluoroalkyl, alkoxy, and fluoroalkoxy having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy having from 1 to 10 carbon atoms, nitro, acyl, halogen and aryl having from 6 to 10 carbon atoms. $R^1$, $R^2$, and $R^3$ can be connected to form rings. $R^{4,8}$ are individually selected from the group consisting of alkyl and fluoroalkyl having from 1 to 10 carbon atoms, and aryl having from 6 to 10 carbon atoms. Preferably, $R^{4,8}$ contains 2 or 3 carbon atoms, thus making a five- or six-member coordinating ring to the metal center; $R^{5-7,9-11}$ are individually selected from the group consisting of alkyl and fluoroalkyl having from 1 to 10 carbon atoms, cycloaliphatic and aryl having from 4 to 10 carbon atoms, and they can be connected to form a ring containing carbon, oxygen, or nitrogen atoms. In addition, groups $R^4$, $R^5$, $R^6$ or $R^7$ can be connected to $R^8$, $R^9$, $R^{10}$ or $R^{11}$ of the same diketimine ligand or to $R^4$, $R^5$, $R^6$, $R^7$, $R^8$, $R^9$, $R^{10}$ or $R^{11}$ of the other diketimine ligand. Similarly, $R^8$, $R^9$, $R^{10}$ or $R^{11}$ can be connected to the same groups in the other ligand. $R^1$ can also be attached to $R^8$, $R^9$, $R^{10}$ or $R^{11}$ and $R^3$ can be attached to $R^4$, $R^5$, $R^6$ or $R^7$.

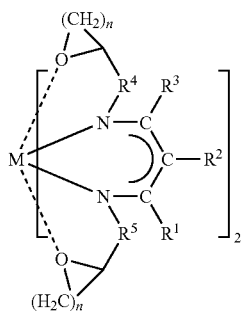

E wherein M is a Group 2 metal selected from the group consisting of magnesium, calcium, strontium, barium or radium, preferably strontium and barium. A variety of organo groups may be employed as for example wherein $R^{1,3}$ is selected from the group consisting of hydrogen, alkyl, fluoroalkyl, alkoxy and fluoroalkoxy having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy having from 1 to 10 carbon atoms, nitro, acyl, halogen and aryl having from 6 to 10 carbon atoms. $R^1$, $R^2$ and $R^3$ can be connected to form rings $R^{4,5}$ are individually selected from the group consisting of alkyl having from 1 to 10 carbon atoms, preferably $R^{4,5}$ contains 1 or 2 carbon atoms, thus making a five- or six-member coordinating ring to the metal center; n=3, 4, 5. In addition, $R^4$ can be connected to $R^5$ of the same ligand or to $R^4$ or $R^5$ of the other ligand. Similarly, $R^5$ can be connected to the same group of the other ligand. $R^1$ can also be attached to $R^2$ or $R^5$ and $R^3$ can be attached to $R^2$ or $R^4$.

For the structures A through E above it is also possible for the β-diketimine ligands to be asymmetric such that the groups attached to one of the diketimine nitrogens, as described above in A-E is different for the corresponding group, also described above in A-E, attached to the other diketimine nitrogen. Two such asymmetric ligands can be complexed to a metal center to form a metal complex or, alternately, two different asymmetric ligands can be complexed to a metal center to form a metal complex. Alternatively, two different symmetric ligands can be complexed to a metal center to form a metal complex.

F wherein M is a Group 2 metal selected from the group consisting of magnesium, calcium, strontium, barium, or radium, preferably strontium and barium. A variety of organo groups may be employed as for example wherein $R^{1,3}$ is selected from the group consisting of hydrogen, alkyl, fluoroalkyl, alkoxy, and fluoroalkoxy having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy having from 1 to 10 carbon atoms, nitro acyl, halogen and aryl having from 6 to 10 carbon atoms. $R^1$, $R^2$ and $R^3$ can be connected to form rings. $R^{4+}5$ are individually selected from the group consisting of alkyl having from 1 to 10 carbon atoms, preferably $R^{4,5}$ contains 2 or carbon atoms, thus making a five- or six-member coordinating ring to the metal center; Alternatively, $R^4$ can also contain ether or amine groups which can also coordinate to the metal center. $R^6$ is selected from the group consisting of alkyl, fluoroalkyl, cycloaliphatic, aryl. In addition $R^1$ can be attached to $R^4$, $R^2$, $R^3$, $R^4$, $R^5$ or $R^6$; $R^6$ can be attached to $R^1$, $R^2$, $R^4$, $R^5$ or $R^6$.

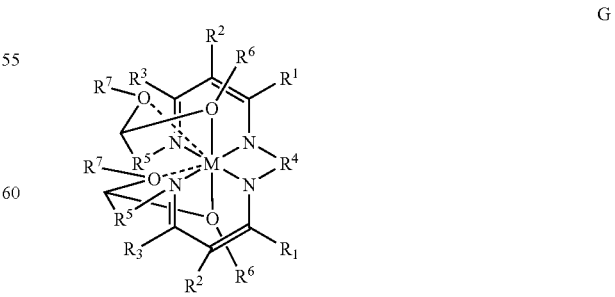

G wherein M is a Group 2 metal selected from the group consisting of magnesium, calcium, strontium, barium or radium, preferably strontium and barium. A variety of organo groups may be employed as for example wherein $R^{1,3}$ is selected from the group consisting of hydrogen, alkyl, fluoroalkyl, alkoxy, and fluoroalkoxy having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy having from 1 to 10 carbon atoms, nitro, acyl, halogen and aryl having from 6 to 10 carbon atoms; $R^{4,5}$ are individually selected from the group consisting of alkyl having from 1 to 10 carbon atoms, preferably $R^{4,5}$ contains 2 or 3 carbon atoms, thus making a five- or six-member coordinating ring to the metal center; Alternatively, $R^4$ can also contain ether or amine groups which can also coordinate to the metal center. $R^{6,7}$ are selected from the group consisting of alkyl, fluoroalkyl, cycloaliphatic, and aryl. In addition, $R^1$ can be attached to $R^2$, $R^3$, $R^4$, $R^5$, $R^7$ and $R^1$, $R^2$ and $R^3$ can be connected into ring structures

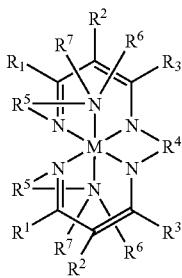

H wherein M is a Group 2 metal selected from the group consisting of magnesium, calcium, strontium, barium or radium, preferably strontium and barium. A variety of organo groups may be employed as for example wherein $R^{1,3}$ is selected from the group consisting of hydrogen, alkyl, fluoroalkyl, alkoxy and fluoroalkoxy having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy having from 1 to 10 carbon atoms, nitro, acyl, halogen and aryl having $R^2$ and $R^3$ can be connected $R^{4,5}$ are individually selected from the group consisting of alkyl having from 1 to 10 carbon atoms, preferably $R^4$$5$ contains 2 or 3 carbon atoms, thus making a five- or six-member coordinating ring to the metal center. Alternatively, $R^4$ can also contain ether or amine groups which can also coordinate to the metal center. $R^{6,7}$ are selected from the group consisting of alkyl, fluoroalkyl, cycloaliphatic, aryl. $R^3$ can be connected to $R^1$, $R^2$, $R^4$, $R^5$, $R^6$, $R^7$.

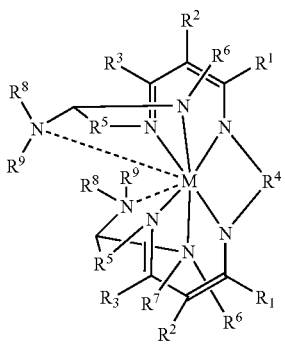

I wherein M is a Group 2 metal selected from the group consisting of magnesium, calcium, strontium, barium or radium, preferably strontium and barium. A variety of organo groups may be employed as for example wherein $R^{1,3}$ is selected from the group consisting of hydrogen, alkyl, fluoroalkyl, alkoxy, and fluoroalkoxy having from 1 to 10 carbon atoms, preferably a group containing 1 to 6 carbon atoms, cycloaliphatic and aryl, having from 4 to 10 carbon atoms; $R^2$ is selected from the group consisting of hydrogen, alkyl and alkoxy, nitro, acyl, halogen and aryl having from 1 to 10 carbon atoms; $R^{4,5}$ are individually selected from the group consisting of alkyl having from 1 to 10 carbon atoms, preferably $R^{4,5}$ contains 2 or 3 carbon atoms, thus making a five- or six-member coordinating ring to the metal center. Alternatively, $R^4$ can also contain ether or amine groups which can also coordinate to the metal center. $R^6$-9 are individually selected from the group consisting of alkyl and fluoroalkyl having from 1 to 10 carbon atoms, cycloaliphatic and aryl having from 4 to 10 carbon atoms.

In addition to the above complexes, while not wishing to be bound by theory, mixed Group 2 metal, preferably barium, complexes can also be made where two different diketimine anions are coordinated to one metal center or where one diketiminate anion and one other organic or inorganic anion coordinate to the Group 2 metal to make a complete complex. Examples of such alternative anions include, but are not limited to, pyrrolyls, imidazolates, beta-diketonates, acetates, ketoiminates, $C_{1-10}$ alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, $C_{1-10}$ alkyl, silylalkyl, fluoroalkyl, and $C_{4-12}$ aryl.

Mixed ligands of diketimine and other ligands are also contemplated such as a metal complex composition having a structure comprising;

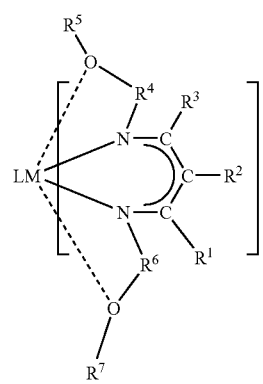

A' wherein M is a Group 2 metal selected from the group consisting of magnesium, calcium, strontium, barium or radium, and mixtures thereof; $R^{1,3}$ are individually selected from the group consisting of hydrogen, alkyl and fluoroalkyl, having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, or halogen and aryl having from 4 to 10 carbon atoms; $R^{4,6}$ are individually selected from the group consisting of alkyl and fluoroalkyl having from 1 to 10 carbon atoms, and aryl having from 4 to 10 carbon atoms; $R^{5,7}$ are selected from the group consisting of alkyl and fluoroalkyl having from 1 to 10 carbon atoms, cycloaliphatic and aryl having from 4 to 10 carbon atoms; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl; or

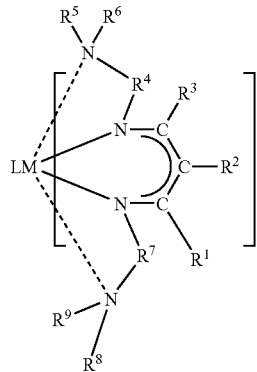

B' wherein M is a Group 2 metals selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 6 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl; or,

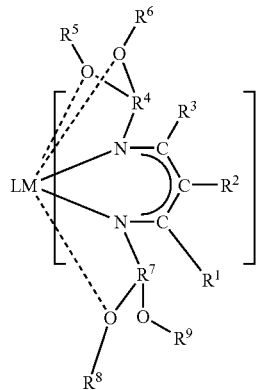

C' wherein M is a Group 2 metals selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 4 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl; or,

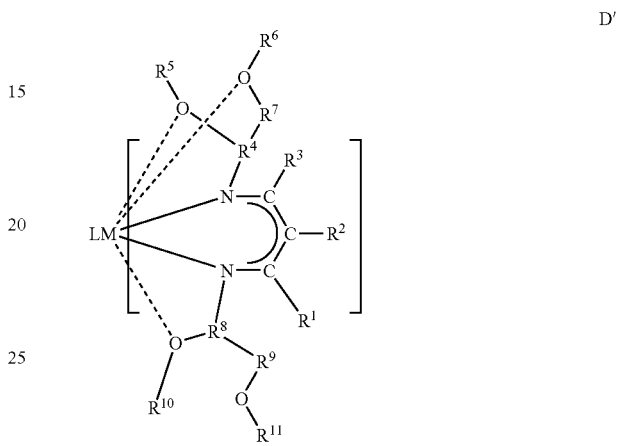

D' wherein M is a Group 2 metal selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,8}$ are individually selected from the group consisting of alkyl and fluoroalkyl having from 1 to 10 carbon atoms and aryl having from 4 to 10 carbon atoms; $R^{5-7,9-11}$ are individually selected from the group consisting of alkyl and fluoroalkyl having from 1 to 10 carbon atoms, cycloaliphatic and aryl having from 4 to 10 carbon atoms; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl; and,

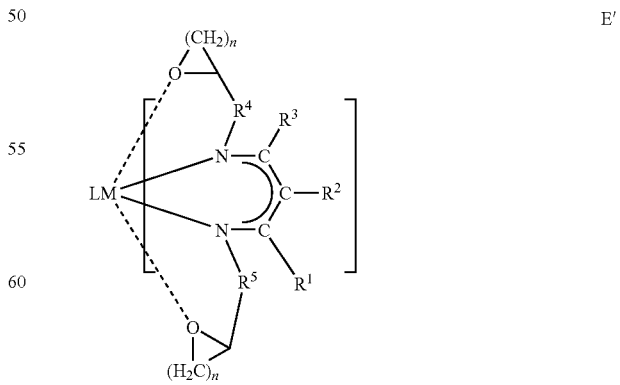

E' wherein M is a Group 2 metal selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,5}$ are individually selected from the group consisting of alkyl having from 1 to 10 carbon atoms; n=3, 4, 5; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl.

The compositions of the Present Invention may also be mixed β-diketiminate ligands complexed with a metal, M, wherein M is a Group 2 metal selected from the group consisting of magnesium, calcium, strontium, barium and radium; bonded through the open bonds shown to the left of any two different ligands selected from the group consisting of;

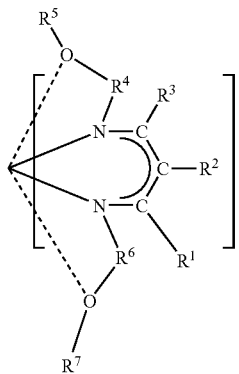

A″ wherein $R^{1,3}$ are individually selected from the group consisting of hydrogen, alkyl and fluoroalkyl, having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,6}$ are individually selected from the group consisting of alkyl and fluoroalkyl having from 1 to 10 carbon atoms, and aryl having from 4 to 10 carbon atoms; $R^{5,7}$ are selected from the group consisting of alkyl and fluoroalkyl having from 1 to 10 carbon atoms, cycloaliphatic and aryl having from 4 to 10 carbon atoms; silylalkyl, fluoroalkyl, and aryl;

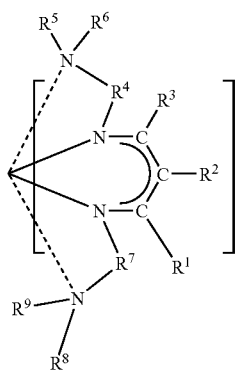

B″ wherein $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 6 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms;

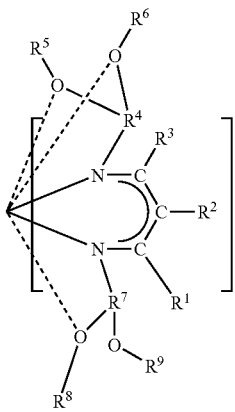

C″ wherein $R^{1,3}$ are individually selected from the group consisting of hydrogen, alkyl and fluoroalkyl having from 1 to 10 carbon atoms, cycloaliphatic and aryl having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 4 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms;

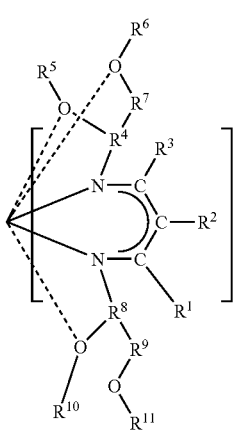

D″ wherein $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,8}$ are individually selected from the group consisting of alkyl and fluoroalkyl having from 1 to 10 carbon atoms and aryl having from 4 to 10 carbon atoms; $R^{5-7,9-11}$ are individually selected from the group consisting of alkyl and fluoroalkyl having from 1 to 10 carbon atoms, cycloaliphatic and aryl having from 4 to 10 carbon atoms; and,

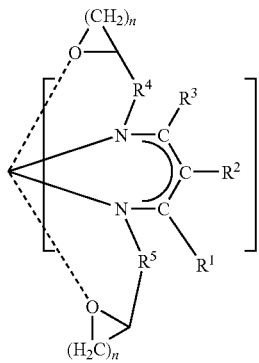

wherein $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,5}$ are individually selected from the group consisting of alkyl having from 1 to 10 carbon atoms; n=3, 4, 5

These Group 2 metal complexes, based upon polydentate β-diketiminate ligands, can be utilized as potential precursors to prepare metal oxide films via either the chemical vapor deposition (CVD), molecular layer deposition (MLD), or atomic layer deposition (ALD) method at temperatures less than 600° C. with oxidizing agents such as water, ozone, oxygen, oxygen plasma, nitrous oxide or combinations thereof. For multi-component metal oxide, these complexes can be premixed as source materials. These metal-containing complexes with polydentate β-diketiminate ligands can be delivered in vapor phase into a CVD or ALD reactor via well-known bubbling or vapor draw techniques. A direct liquid injection can also be employed by dissolving the complexes in a suitable solvent or a solvent mixture to prepare a solution with a molar concentration from 0.001 to 2 M depending the solvent or mixed-solvents employed.

The solvent employed to solubilize the precursor for use in a deposition process may comprise any compatible solvent or mixtures of solvent including aliphatic hydrocarbons, aromatic hydrocarbons, ethers, amines, esters, nitrites, amides and alcohols. The solvent component of the solution preferably comprises a solvent selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown ethers, $C_2$-$C_{20}$ amides; $C_6$-$C_{12}$ aliphatic hydrocarbons; $C_6$-$C_{18}$ aromatic hydrocarbons; organic esters; organic amines, polyamines, organic amides and linear or cyclic amine-ether solvents such as $Me_2NCH_2CH_2OCH_2CH_2NMe_2$.

Another class of solvents that offers advantages is the organic amide class of the form RCONR'R" wherein R and R' are alkyl having from 1-10 carbon atoms and they can be connected to form a cyclic group $(CH_2)_n$, wherein n is from 4-6, preferably 5, and R" is selected from alkyl having from 1 to 4 carbon atoms and cycloalkyl. N-methyl and N-cyclohexyl-2-pyrrolidinones, N,N-Diethylacetamide, and N,N-Diethylformamide are examples.

Several advantages can be achieved through these metal-containing polydentate β-diketiminates as precursors for chemical vapor deposition or atomic layer deposition, and these include:

an ability to form reactive complexes in good yield;

an ability to form monomeric complexes, particularly strontium and barium complexes by complexing with diketiminatof ligands, thus achieving higher vapor pressure than that of the known strontium and barium precursors. The known strontium and barium precursors are typically polymeric complexes with extremely low vapor pressure.

an ability to form highly conformal metal oxide thin films when used as volatile precursors for CVD and ALD deposition for use in microelectronic devices;

an ability to enhance the surface reaction between the metal-containing polydentate β-diketiminates and the surface of a substrate due to the high chemical reactivity of the complexes;

an ability to tune the physical and chemical properties of these metal-containing polydentate β-diketiminates via a change in the $R^{1-9}$ groups;

additionally, metal complexes can also be made by coordinating two different carefully chosen diketimnate anions to a metal center, such as barium, such that the two ligands experience an optimal 'fit' or 'interlock' with each other and around the metal in such a way as to provide an adequate coordination sphere to create a stable monomeric complex; and, a novel and practical process for the synthesis of new diketiminate ligands avoiding the use of toxic alkylating agents.

The present invention is also a process for synthesizing diketimine ligands without the use of toxic alkylating agents comprising the following steps:

(1) reacting a primary amine with a beta-diketone to yield a ketoimine ligand;

(2) lithiating the same or different primary amine;

(3) trialkysilylating the lithiated primary amine to give a trialkylsily amine;

(4) repeating the lithiation/trialkylsilylaltion steps to yield a bis(trialkylsily)amine;

(5) the ketoimine ligand of step (1) is mixed with the bis(trialkylsilyl)amine of step (2) and a strong acid;

(6) the reaction mixture is then treated with a solution of a base; and (7) the diketimine ligand is then isolated from the reaction mixture by vacuum distillation.

EXAMPLE 1

Synthesis of bis(trimethylsilyl)aminoacetaldehyde dimethylacetal

Under a nitrogen atmosphere, 5.25 g (0.05 moles) of aminoacetaldehyde dimethylacetal were dissolved in 50 ml of dry tetrahydrofuran and cooled to −78° C. 20 ml of 2.5M nBuLi (0.05 moles) were then added over 5 minutes with stirring. The mixture was then stirred for 15 minutes at −78 C then allowed to slowly warm to room temperature. 6.3 ml (0.05 moles) of chlorotrimethylsilane were then added over 20 minutes and the reaction allowed to stir for an additional 30 minutes. During this addition the mixture increased in temperature and a precipitate of lithium chloride was observed to form. The mixture was then cooled back down to −78 C and an additional 20 ml of 2.5M nBuLi added over 5 minutes with stirring and the mixture was held at this temperature for an additional 15 minutes before being allowed to warm back up to room temperature. An additional 6.3 ml of chlorotrimethylsilane was then added over a 20 minute period with stirring, during which time the mixture was observed to warm up and additional lithium chloride form. The Mixture was then stirred for an additional 30 minutes before being filtered. The tetrahydrofuran was then removed from the filtrate by vacuum and the final product was vacuum distilled from the remaining filtrate. This resulted in a yield of 8.0 g (64% of theoretical) of $(Me_3Si)_2NCH_2CH(OMe)_2$.

$^1$H NMR: (500 MHz, $C_6D_6$): δ=0.21 (s, 18H), δ=3.05 (d, 2H), δ=3.16 (s, 6H), δ=4.12 (t, 1H).

GCMS parent ion at 249 mu.

EXAMPLE 2

Synthesis of
4-(2,2-bis(methoxy)ethylamino)-3-penten-2-one 21.0 g of aminoacetaldehyde dimethylacetal (0.2 moles) were dissolved into 100 ml of tetrahydrofuran to which 20.0 g of 2,4-pentanedione (0.2 moles) were added dropwise over 5 minutes. The resulting mixture was then stirred overnight after which time the solvent and water of condensation formed during the reaction was removed by vacuum distillation. The final product was then vacuum distilled as a clear liquid. Yield of $MeC(O)CH_2C(NCH_2CH(OMe)_2)Me$=25.0 g (72% of theoretical).

$^1$H NMR: (500 MHz, $C_6D_6$): δ=1.47 (s, 3H), δ=2.00 (d, 3H), δ=2.98 (t, 2H), δ=3.05 (s, 6H), δ=4.00 (t, 1H), δ=4.89 (s, 1H), δ=11.2 (bs, 1H)

GCMS parent ion at 211 mu.

EXAMPLE 3

Synthesis of N-(2,2-bis(methoxy)ethyl)-4-(2,2-bis(methoxy)ethylimino)-2-penten-2-amine 8.0 g (0.032 moles) of bis(trimethylsilyl)aminoacetaldehyde dimethylacetal were mixed with 4.0 g (0.021 moles) of 4-(2,2-bis(methoxy)ethylamino)-3-penten-2-one. To this mixture was added 4.37 g (0.0266 moles) of pentafluoropropionic acid dropwise over 5 minutes with rapid stirring. The mixture darkened and became warm, eventually forming two immiscible layers, and was allowed to stir for 1 hour. 2.56 g (0.0266 moles) of sodium t-butoxide dissolved in 5 ml of tetrahydrofuran was then added dropwise over a five minute period. The mixture warmed and became one liquid phase which was yellow. The solvent was then removed by vacuum distillation at room temperature and the product then vacuum distilled out of the resulting residue as a clear liquid by heating>150° C. Yield of $MeC(NCH_2CH(OMe)_2)CHC(HNCH_2CH(OMe)_2)Me$=5.26 g (90% of theoretical).

$^1$H NMR: (500 MHz, $C_6D_6$): δ=1.68 (s, 6H), δ=3.25 (s, 12H), δ=3.44 (d, 4H), δ=4.58 (s 1H), δ=4.60 (t, 2H), δ=11.5 (bs 1H).

GCMS parent ion at 249 mu

EXAMPLE 4

Synthesis of bis(N-(2,2-bis(methoxy)ethyl)-4-(2,2-bis(methoxy)ethylimino)-2-penten-2-aminato) barium Under an atmosphere of nitrogen, 1.354 g (0.002 moles) of barium hexamethyldisilazide tetrahydrofuranate were dissolved in 5 ml of dry tetrahydrofuran and slowly added to 1.236 g (0.004 moles) of N-(2,2-bis(methoxy)ethyl)-4-(2,2-bis(methoxy)ethylimino)-2-penten-2-amine stirring in 10 ml of tetrahydrofuran. The mixture became yellow colored and was stirred overnight. The volatiles were then removed by application of vacuum and he resulting oil dissolved in 5 ml of dry hexane. The resulting solution was then allowed to stand at −20 C for 2 hours to crystallize out the product.

Yield=0.7 g (45% of theoretical)

$^1$H NMR: (500 MHz, $C_6D_6$): δ=1.99 (s, 12H), δ=3.29 (s, 24H), δ=3.64 (t, 8H), δ=4.27 (t, 4H), δ=4.52 (s, 2H).

A colorless crystal of bis(N-(2,2-bis(methoxy)ethyl)-4-(2,2-bis(methoxy)ethylimino)-2-penten-2-aminato) barium was structurally characterized by X-ray single crystal analysis (see FIG. 1). The structure in FIG. 1 shows the barium atom is coordinated with two N-(2,2-bis(methoxy)ethyl)-4-(2,2-bis(methoxy)ethylimino)-2-penten-2-aminato ligands with a coordination number of nine, i.e. four nitrogen atoms and five oxygen atoms, leaving three methoxy groups dangling uncoordinated to the metal center.

EXAMPLE 5

Synthesis of
N,N-Bis(trimethylsilyl)-2-methoxyethylamine

Under a nitrogen atmosphere, 7.5 g (0.1 moles) of 2-Methoxyethylamine were dissolved in 100 ml of dry tetrahydrofuran and cooled to −78° C. 40 ml of 2.5M nBuLi (0.05 moles) were then added over 5 minutes with stirring. The mixture was then stirred for 15 minutes at −78 C then allowed to slowly warm to room temperature. 12.5 ml (0.1 moles) of chlorotrimethylsilane were then added over 20 minutes and the reaction allowed to stir for an additional 30 minutes. During this addition, the mixture increased in temperature, and a precipitate of lithium chloride was observed to form. The mixture was then cooled back down to −78 C, and an additional 40 ml of 2.5M nBuLi added over 5 minutes with stirring. The mixture was held at this temperature for an additional 15 minutes before being allowed to warm back up to room temperature. An additional 12.5 ml of chlorotrimethylsilane was then added over a 20 minute period with stirring, during which time the mixture was observed to warm up and additional lithium chloride formed. The mixture was then stirred for an additional 30 minutes before being filtered. The tetrahydrofuran was then removed from the filtrate by vacuum, and the final product was vacuum distilled from the remaining filtrate. This resulted in a yield of 13.1 g (60% of theoretical) of $(Me_3Si)_2NCH2CH2OMe$.

$^1$H NMR: (500 MHz, $C_6D_6$): δ=0.16 (s, 18H), δ=3.04 (t, 2H), δ=3.11 (s, 3H), δ=3.19 (t, 2H).

GCMS parent ion at 219 mu.

EXAMPLE 6

Synthesis of
4-(2-methoxyethylamino)-3-penten-2-one 7.50 g of 2-Methoxyethylamine (0.1 moles) were dissolved into 100 ml of tetrahydrofuran to which 10.0 g of 2,4-pentanedione (0.1 moles) were added dropwise over 5 minutes. The resulting mixture was then stirred overnight after which time the solvent and water of condensation formed during the reaction was removed by vacuum distillation. The final product was then vacuum distilled as a clear liquid. Yield of $MeC(O)CH_2C(NCH_2CH_2OMe)Me$=11.8 g (75% of theoretical).

$^1$H NMR: (500 MHz, C$_6$D$_6$): δ=1.48 (s, 3H), δ=2.00 (s, 3H), δ=2.82 (q, 2H), δ=2.92 (q, 2H), δ=2.95 (s, 3H), δ=4.88 (s, 1H), δ=11.2 (bs, 1H).

GCMS parent ion at 157 mu.

EXAMPLE 7

Synthesis of N-(2-methoxyethyl)-4-(2-methoxyethylimino)-2-penten-2-amine 6.56 g (0.03 moles) of N,N-Bis(trimethylsilyl)-2-methoxyethylamine were mixed with 3.14 g (0.02 moles) of 4-(2-methoxyethylamino)-3-penten-2-one. To this mixture was added 4.1 g (0.026 moles) of pentafluoropropionic acid dropwise over 5 minutes with rapid stirring. The mixture darkened and became warm, eventually forming two immiscible layers, and was allowed to stir for 1 hour. 2.5 g (0.0266 moles) of sodium t-butoxide dissolved in 5 ml of tetrahydrofuran was then added dropwise over a five minute period. The mixture warmed and became one liquid phase, which was yellow. The solvent was then removed by vacuum distillation at room temperature, and the product then vacuum distilled out of the resulting residue as a clear liquid by heating>150° C. Yield of MeC(NCH$_2$CHOMe)CHC(HNCH$_2$CH$_2$OMe)Me=3.9 g (91% of theoretical).

$^1$H NMR: (500 MHz, C$_6$D$_6$): δ=1.68 (s, 6H), δ=3.18 (s, 6H), δ=3.17 (t, 4H), δ=3.45 (t, 4H), δ=4.58 (s, 1H), δ=11.5 (bs 1H).

GCMS parent ion at 214 mu

EXAMPLE 8

Synthesis of bis(N-(2-methoxyethyl)-4-(2-methoxyethylimino)-2-penten-2-aminato) barium Under an atmosphere of nitrogen, 1.282 g (0.00213 moles) of barium hexamethyldisilazide tetrahydrofuranate were dissolved in 5 ml of dry tetrahydrofuran and slowly added to 0.913 g (0.00426 moles) of N-(2-methoxyethyl)-4-(2-methoxyethylimino)-2-penten-2-amine, stirring in 10 ml of tetrahydrofuran. The mixture became yellow colored and was stirred overnight. The volatiles were then removed by application of vacuum, and the resulting oil dissolved in 5 ml of dry hexane. The resulting solution was then allowed to stand at −20 C for 2 hours to crystallize out the product.

Yield=0.75 g (63% of theoretical)

$^1$H NMR: (500 MHz, C$_6$D$_6$): δ=1.99 (s, 12H), δ=3.26 (t, 8H), δ=3.28 (s, 12H), δ=3.48 (t, 8H), δ=4.5 (s, 2H).

EXAMPLE 9

Synthesis of N,N-Bis(trimethylsilyl)-2-(N',N'-dimethylamino)ethylamine

This molecule was made according to the following procedure. Under a nitrogen atmosphere, 8.5 g (0.1 moles) of N,N-Dimethylethylenediamine were dissolved in 100 ml of dry tetrahydrofuran and cooled to −78° C. 40 ml of 2.5M nBuLi (0.05 moles) were then added over 5 minutes with stirring. The mixture was then stirred for 15 minutes at −78 C then allowed to slowly warm to room temperature. 12.5 ml (0.1 moles) of chlorotrimethylsilane were then added over 20 minutes and the reaction allowed to stir for an additional 30 minutes. During this addition, the mixture increased in temperature, and a precipitate of lithium chloride was observed to form. The mixture was then cooled back down to −78 C, and an additional 40 ml of 2.5M nBuLi added over 5 minutes with stirring. The mixture was held at this temperature for an additional 15 minutes, before being allowed to warm back up to room temperature. An additional 12.5 ml of chlorotrimethylsilane was then added over a 20 minute period with stirring, during which time the mixture was observed to warm up and additional lithium chloride form. The mixture was then stirred for an additional 30 minutes before being filtered. The tetrahydrofuran was then removed from the filtrate by vacuum and the final product was vacuum distilled from the remaining filtrate. This resulted in a yield of 15.0 g (65% of theoretical) of (Me$_3$Si)$_2$NCH$_2$CH(NMe)$_2$.

$^1$H NMR: (500 MHz, C$_6$D$_6$): δ=0.17 (s, 18H), δ=2.1 (s, 6H), δ=2.26 (m, 2H), δ=2.98 (m, 2H).

GCMS parent ion at 232 mu.

EXAMPLE 10

Synthesis of 4-(2-(N,N-dimethylamino)ethylamino)-3-penten-2-one 17.0 of N,N-Dimethylaminoethylenediamine (0.2 moles) were dissolved into 100 ml of tetrahydrofuran to which 20.0 g of 2,4-pentanedione (0.2 moles) were added dropwise over 5 minutes. The resulting mixture was then stirred overnight after which time the solvent and water of condensation formed during the reaction was removed by vacuum distillation. The final product was then vacuum distilled as a clear liquid. Yield of MeC(O)CH$_2$C(NCH$_2$CH$_2$NMe$_2$)Me=11.9 g (70% of theoretical).

EXAMPLE 11

Synthesis of N-(2-(N,N-dimethylamino)ethyl)-4-(2-(N,N-dimethylamino)ethylimino)-2-penten-2-amine 3.48 g (0.015 moles) of N,N-Bis(trimethylsilyl)-2-(N',N'-dimethylamino)ethylamine were mixed with 1.7 g (0.01 moles) of 4-(2-(N,N-dimethylamino)ethylamino)-3-penten-2-one. To this mixture was added 1.64 g (0.0125 moles) of pentafluoropropionic acid dropwise over 5 minutes with rapid stirring. The mixture darkened and became warm, eventually forming two immiscible layers, and was allowed to stir for 1 hour. 0.98 g (0.0125 moles) of sodium t-butoxide dissolved in 5 ml of tetrahydrofuran was then added dropwise over a five minute period. The mixture warmed and became one liquid phase, which was yellow. The solvent was then removed by vacuum distillation at room temperature, and the product then vacuum distilled out of the resulting residue as a clear liquid by heating >150° C. Yield of MeC(NCH$_2$CH$_2$NMe$_2$)CHC(HNCH$_2$CH$_2$NMe$_2$)Me=2.05 g (85% of theoretical).

$^1$H NMR: (500 MHz, C$_6$D$_6$): δ=1.72 (s, 6H), δ=2.17 (s, 12H), δ=2.51 (t, 4H), δ=3.28 (t 4H), δ=4.60 (s, 1H), δ=11.4 (bs, 1H).

GCMS parent ion at 240 mu

EXAMPLE 12

Synthesis of bis(N-(2-(N,N-dimethylamino)ethyl)-4-(2-(N,N-dimethylamino)ethylimino)-2-penten-2-aminato) barium Under an atmosphere of nitrogen, 1.3 g (0.002 moles) of barium hexamethyldisilazide tetrahydrofuranate were dissolved in 5 ml of dry tetrahydrofuran and slowly added to 1.04 g (0.004 moles) of N-(2-(N,N-dimethylamino)ethyl)-4-(2-(N,N-dimethylamino)ethylimino)-2-penten-2-amine stirring in 10 ml of tetrahydrofuran. The mixture became yellow colored and was stirred overnight. The volatiles were then removed by application of vacuum and he resulting oil dissolved in 5 ml of dry hexane. The resulting solution was then allowed to stand at −20 C for 2 hours to crystallize out the product.

Yield=1.0 g (75% of theoretical)

$^1$H NMR: (500 MHz, $C_6D_6$): δ=1.9 (s, 12H), δ=2.14 (s, 24H), δ=2.4 (t, 8H), δ=3.3 (t, 8H), δ=4.64 (s, 2H).

EXAMPLE 13

Synthesis of bis(N-(2,2-bis(methoxy)ethyl)-4-(2,2-bis(methoxy)ethylimino)-2-penten-2-aminato) strontium To a solution of 1.00 g (1.82 mmol) of strontium hexamethyldisilazide tetrahydrofuranate in 10 mL tetrahydrofuran (THF) was added 1.00 g (3.64 mmol) of N-(2,2-bis(methoxy)ethyl)-4-(2,2-bis(methoxy)ethylimino)-2-penten-2-amine in 10 mL THF. The resulting solution was stirred at room temperature for 16 hours. All volatiles were removed under vacuum to provide a viscous tan oil. 1.34 g of beige solid was obtained after further work-up.

$^1$H NMR (500 MHz, $C_6D_6$): δ=4.52 (s, 1H), 4.28 (t, 2H), 3.67 (d, 3H), 3.31 (s, 12H), 2.01 (s, 6H)

EXAMPLE 14

Synthesis of bis(N-(2-(N,N-dimethylamino)ethyl)-4-(2-(N,N-dimethylamino)ethylimino)-2-penten-2-aminato) strontium To a solution of 0.76 g (1.38 mmol) of strontium hexamethyldisilazide tetrahydrofuranate in 10 mL THF was added 0.66 g (2.75 mmol) of N-(2-(N,N-dimethylamino)ethyl)-4-(2-(N,N-dimethylamino)ethylimino)-2-penten-2-amine in 10 mL THF. The solution was refluxed for 16 hours, after which all volatiles were pumped off under vacuum to give rise to a waxy brown yellow solid weighing 0.90 g.

The invention claimed is:

1. A metal complex composition having a structure comprising;

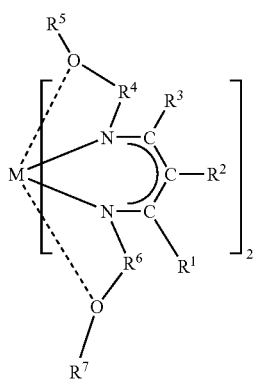

A wherein M is a Group 2 metal selected from the group consisting of magnesium, calcium, strontium, barium or radium, and mixtures thereof; $R^{1,3}$ are individually selected from the group consisting of hydrogen, alkyl and fluoroalkyl, having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,6}$ are individually selected from the group consisting of alkyl and fluoroalkyl having from 1 to 10 carbon atoms, and aryl having from 4 to 10 carbon atoms; $R^{5,7}$ are selected from the group consisting of alkyl and fluoroalkyl having from 1 to 10 carbon atoms, cycloaliphatic and aryl having from 4 to 10 carbon atoms; or

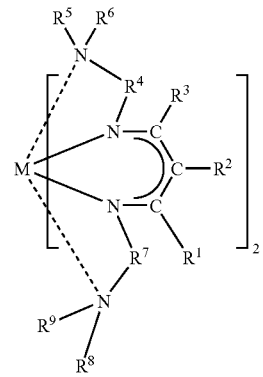

B wherein M is a Group 2 metals selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 6 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms; or,

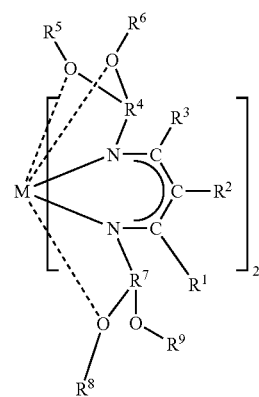

C wherein M is a Group 2 metals selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 4 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms; or,

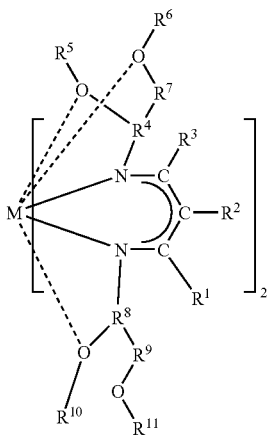

D wherein M is a Group 2 metal selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,8}$ are individually selected from the group consisting of alkyl and fluoroalkyl having from 1 to 10 carbon atoms and aryl having from 4 to 10 carbon atoms; $R^{5-7,9-11}$ are individually selected from the group consisting of alkyl and fluoroalkyl having from 1 to 10 carbon atoms, cycloaliphatic and aryl having from 4 to 10 carbon atoms; or,

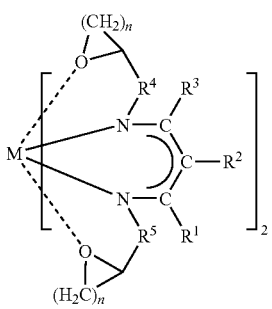

E wherein M is a Group 2 metal selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,5}$ are individually selected from the group consisting of alkyl having from 1 to 10 carbon atoms; n=3, 4, 5 or,

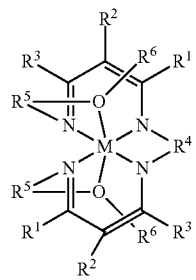

F wherein M is a Group 2 metal selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 6 to 10 carbon atoms; $R^{4,5}$ are individually selected from the group consisting of alkyl having from 1 to 10 carbon atoms; or,

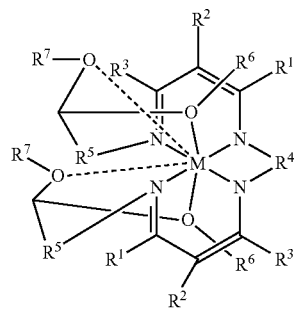

G wherein M is a Group 2 metal selected from the group consisting of magnesium, calcium, strontium, barium or radium; $R^{1,3}$ is selected from the group consisting of alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 6 to 10 carbon atoms; $R^{4,5}$ are selected from the group consisting of alkyl having from 1 to 10 carbon atoms; $R^{6,7}$ are individually selected from the group consisting of alkyl and fluoroalkyl having from 1 to 10 carbon atoms, cycloaliphatic and aryl having from 4 to 10 carbon atoms; or,

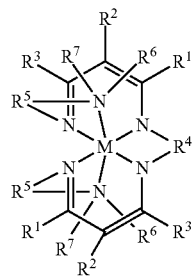

H wherein M is a Group 2 metal selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 6 to 10 carbon atoms; $R^{4,5}$ are individually selected from the group consisting of alkyl having from 1 to 10 carbon atoms; or,

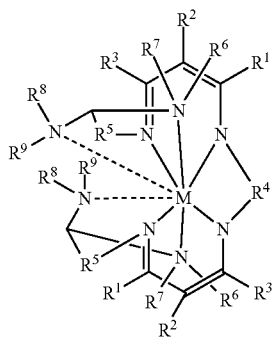

wherein M is a Group 2 metal selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 6 to 10 carbon atoms; $R^{4,5}$ are individually selected from the group consisting of alkyl having from 1 to 10 carbon atoms.

2. The composition of claim 1(A) wherein $R^{4,6}$ contains 2 or 3 carbon atoms, making a five- or six-member coordinating ring to the metal center.

3. The composition of claim 1(A) wherein $R^5$ or $R^4$ are connected to $R^6$ and $R^7$ of the same diketimine ligand or to $R^4$, $R^5$, $R^6$ and $R^7$ of the other diketimine ligand.

4. A composition comprising bis(N-(2,2-methoxyethyl)-4-(2,2-methoxyethylimino)-2-penten-2-aminato) barium.

5. A process of depositing a Group 2 metal oxide selected from the group consisting of magnesium, calcium, strontium, barium or radium from a metal complex of claim 1.

6. The process of claim 5 wherein the deposition is selected from the group consisting of chemical vapor deposition, pulsed chemical vapor deposition, molecular layer deposition and atomic layer deposition.

7. The process of claim 5 wherein the deposition is performed at a substrate temp range 50-600° C.

8. The process of claim 5 wherein the deposition is performed in the presence of an oxygen source selected from the group consisting of oxygen, ozone, water vapor, oxygen plasma, nitrous oxide, dinitrogen tetraoxide, nitrogen dioxide or combinations thereof.

9. The process of claim 5 wherein the deposition is performed with a titanium precursor to provide a barium, strontium titanate ternary film.

10. The process of claim 5 wherein the deposition is performed with a titanium precursor to provide a strontium titanate binary film.

11. The process of claim 5 wherein the deposition is performed with a titanium precursor to provide a barium titanate binary film.

12. The process of claim 5 wherein the deposition is performed with a lanthanide precursor to provide a barium doped lanthanate binary film.

13. A process for synthesizing diketimine ligands without the use of toxic alkylating agents comprising the following steps:
(1) reacting a primary amine with a beta-diketone to yield a ketoimine ligand;
(2) lithiating the same or different primary amine;
(3) trialkysilylating the lithiated primary amine to give a trialkylsily amine;
(4) repeating the lithiation/trialkylsilylaltion steps to yield a bis(trialkylsily)amine;
(5) the ketoimine ligand of step (1) is mixed with the bis(trialkylsilyl)amine of step (2) and a strong acid;
(6) the reaction mixture is then treated with a solution of a base; and
(7) the diketimine ligand is then isolated from the reaction mixture by vacuum distillation.

14. The metal containing complex of claim 1 dissolved in a solvent selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown ethers; $C_6$-$C_{12}$ aliphatic hydrocarbons; $C_6$-$C_{18}$ aromatic hydrocarbons; organic esters; organic amines; and polyamines, cyclic or linear etheramines and organic amides.

15. A vapor deposition process for forming a conformal metal oxide thin film on a substrate wherein a solution of precursor source and an oxygen containing agent are introduced to a deposition chamber and a metal oxide film deposited on a substrate, the improvement which comprises using a solution comprised of the metal containing complex of claim 12.

16. A metal complex composition having a structure comprising;
(i) a diketoiminate selected from the group consisting of;

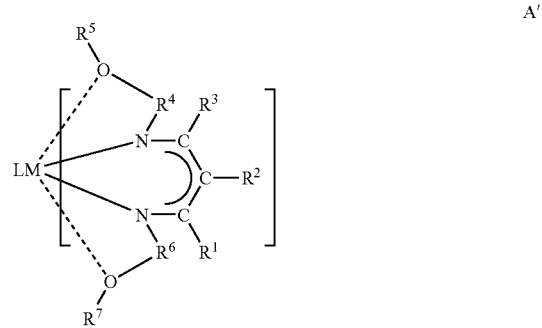

wherein M is a Group 2 metal selected from the group consisting of magnesium, calcium, strontium, barium or radium, and mixtures thereof; $R^{1,3}$ are individually selected from the group consisting of hydrogen, alkyl and fluoroalkyl, having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,6}$ are individually selected from the group consisting of alkyl and fluoroalkyl having from 1 to 10 carbon atoms, and aryl having from 4 to 10 carbon atoms; $R^{5,7}$ are selected from the group consisting of alkyl and fluoroalkyl having from 1 to 10 carbon atoms, cycloaliphatic and aryl having from 4 to 10 carbon atoms; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl; or

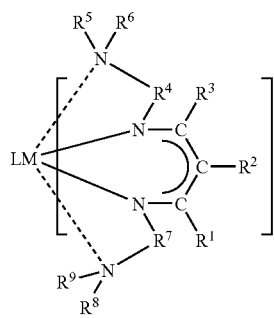

B' wherein M is a Group 2 metals selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 6 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl; or,

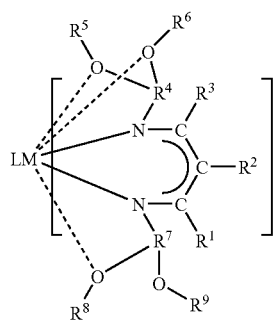

C' wherein M is a Group 2 metals selected from the group consisting of magnesium, calcium, strontium, barium, or radium; $R^{1,3}$ are individually selected from the group consisting of hydrogen, alkyl and fluoroalkyl having from 1 to 10 carbon atoms, cycloaliphatic and aryl having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 4 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl; or,

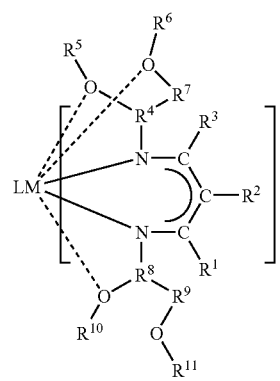

D' wherein M is a Group 2 metal selected from the group consisting of magnesium, calcium, strontium, barium or radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,8}$ are individually selected from the group consisting of alkyl and fluoroalkyl having from 1 to 10 carbon atoms and aryl having from 4 to 10 carbon atoms; $R^{5-7,9-11}$ are individually selected from the group consisting of alkyl and fluoroalkyl having from 1 to 10 carbon atoms, cycloaliphatic and aryl having from 4 to 10 carbon atoms; the second mono anion L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl; and,

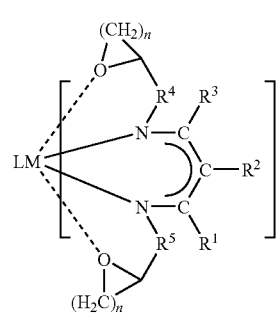

E' wherein M is a Group 2 metal selected from the group consisting of magnesium, calcium, strontium, barium and radium; $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,5}$ are individually selected from the group consisting of alkyl having from 1 to 10 carbon atoms; n=3, 4, 5; the second mono anion L L is selected from the group consisting of pyrrolyls, imidazolates, beta-diketonates, acetates, ketoiminates, alkoxides, amides, hydrides, beta-ketoesters, amidinates, guanidinates, cyclopentadienyl, alkyl substituted cyclopentadienyl, cyanide, isocyanide, formate, oxalate, malonate, phenoxide, thiolate, sulfide, nitrate, alkyl, silylalkyl, fluoroalkyl, and aryl.

17. A metal complex composition having a structure comprising a metal, M, wherein M is a Group 2 metal selected from the group consisting of magnesium, calcium, strontium, barium and radium; bonded to any two different ligands selected from the group consisting of;

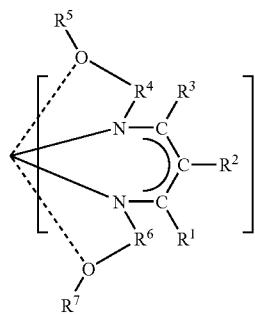

A″ wherein $R^{1,3}$ are individually selected from the group consisting of hydrogen, alkyl and fluoroalkyl, having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,6}$ are individually selected from the group consisting of alkyl and fluoroalkyl having from 1 to 10 carbon atoms, and aryl having from 4 to 10 carbon atoms; $R^{5,7}$ are selected from the group consisting of alkyl and fluoroalkyl having from 1 to 10 carbon atoms, cycloaliphatic and aryl having from 4 to 10 carbon atoms; silylalkyl, fluoroalkyl, and aryl;

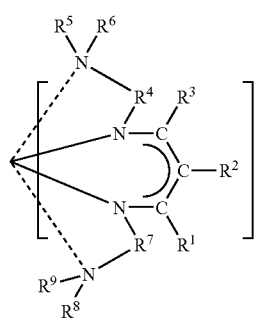

B″ wherein $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 6 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms;

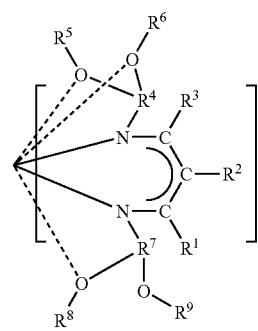

C″ wherein $R^{1,3}$ are individually selected from the group consisting of hydrogen, alkyl and fluoroalkyl having from 1 to 10 carbon atoms, cycloaliphatic and aryl having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,7}$ are individually selected from the group consisting of alkyl and fluoroalkyl having from 1 to 10 carbon atoms, and aryl having from 4 to 10 carbon atoms; $R^{5,6,8,9}$ are individually selected from the group consisting of alkyl and fluoroalkyl having from 1 to 10 carbon atoms, cycloaliphatic and aryl having from 4 to 10 carbon atoms;

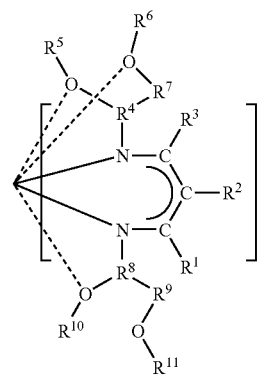

D″ wherein $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,8}$ are individually selected from the group consisting of alkyl and fluoroalkyl having from 1 to 10 carbon atoms and aryl having from 4 to 10 carbon atoms; $R^{5-7,9-11}$ are individually selected from the group consisting of alkyl and fluoroalkyl having from 1 to 10 carbon atoms, cycloaliphatic and aryl having from 4 to 10 carbon atoms; and,

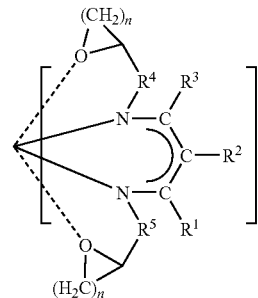

E″ wherein $R^{1,3}$ are individually selected from the group consisting of hydrogen, alkyl and fluoroalkyl having from 1 to 10 carbon atoms, cycloaliphatic and aryl, having from 4 to 10 carbon atoms; $R^2$ is selected from the group consisting of hydrogen, alkyl and alkoxy having from 1 to 10 carbon atoms, nitro, halogen and aryl having from 4 to 10 carbon atoms; $R^{4,5}$ are individually selected from the group consisting of alkyl having from 1 to 10 carbon atoms; n=3, 4, 5.

* * * * *